US012669509B2

(12) United States Patent
Luo

(10) Patent No.: US 12,669,509 B2
(45) Date of Patent: Jun. 30, 2026

(54) MICROPROBE-CAPTURE IN-EMITTER ELUTION-ELECTROSPRAY IONIZATION

(71) Applicant: The Board of Trustees of the Leland Stanford Junior University, Stanford, CA (US)

(72) Inventor: Ruben Yiqi Luo, Redwood City, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 613 days.

(21) Appl. No.: 18/126,891

(22) Filed: Mar. 27, 2023

(65) Prior Publication Data

US 2023/0305019 A1 Sep. 28, 2023

Related U.S. Application Data

(60) Provisional application No. 63/324,573, filed on Mar. 28, 2022.

(51) Int. Cl.
*G01N 33/68* (2006.01)
*H01J 49/16* (2006.01)

(52) U.S. Cl.
CPC ........ *G01N 33/6851* (2013.01); *H01J 49/165* (2013.01)

(58) Field of Classification Search
CPC .......................... H01J 49/165; G01N 33/6851
See application file for complete search history.

(56) References Cited

U.S. PATENT DOCUMENTS

| | | | | |
|---|---|---|---|---|
| 7,928,370 | B2 * | 4/2011 | Amirav | H01J 49/049 |
| | | | | 95/82 |
| 2001/0014461 | A1 * | 8/2001 | Hutchens | B01J 20/288 |
| | | | | 435/7.92 |
| 2002/0150926 | A1 * | 10/2002 | Jindal | G01N 30/463 |
| | | | | 435/7.1 |
| 2011/0305599 | A1 | 12/2011 | Tan et al. | |
| 2015/0233877 | A1 * | 8/2015 | Dovichi | G01N 30/7266 |
| | | | | 250/288 |
| 2015/0346183 | A1 * | 12/2015 | Clarke | G01N 33/6848 |
| | | | | 250/282 |

(Continued)

FOREIGN PATENT DOCUMENTS

WO WO 2015/188282 A1 12/2015

OTHER PUBLICATIONS

Luo et al., "Development of Label-Free Immunoassays as Novel Solutions for the Measurement of Monoclonal Antibody Drugs and Antidrug Antibodies", Clinical Chemistry, 2020, 66:1319-1328.

(Continued)

*Primary Examiner* — Jennifer Wecker
*Assistant Examiner* — Tracy Ching-Tian Colena
(74) *Attorney, Agent, or Firm* — James S. Keddie; Bozicevic, Field & Francis LLP

(57) ABSTRACT

Provided herein is a method for analyzing a molecular interaction. In some embodiments the method may comprise: capturing an analyte on a probe that comprises a binding agent, inserting the probe into the interior capillary of an electrospray emitter, releasing the analyte from the probe while it is in the emitter using an elution liquid, nebulizing the analyte by electrospray; and analyzing the nebulized analyte by mass spectrometry.

17 Claims, 8 Drawing Sheets

BLI Microprobe | Electrospray Emitter (Microprobe-Inserted) | ESI Ion Source | MPIE-ESI-MS Interface Capture Agent | Sample | + | Capture Agent | Analyte

(56)         References Cited

U.S. PATENT DOCUMENTS

| | | | |
|---|---|---|---|
| 2019/0250154 A1* | 8/2019 | Zuk | G01N 33/543 |
| 2020/0365382 A1* | 11/2020 | Arnold | G01N 1/14 |
| 2024/0066115 A1* | 2/2024 | Wong | A61K 39/215 |

OTHER PUBLICATIONS

Luo et al., "Kinetics of Severe Acute Respiratory Syndrome Coronavirus 2 (SARS-CoV-2) Antibody Avidity Maturation and Association with Disease Severity", Clinical Infectious Diseases, 2021, 73:e3095-e3097.

Luo et al., "A SARS-CoV-2 Label-Free Surrogate Virus Neutralization Test and a Longitudinal Study of Antibody Characteristics in COVID-19 Patients", Journal of Clinical Microbiology, 2021, 59(7): e00193-21, 9 pages.

Luo et al., "Using Microprobe-Capture In-Emitter Elution to Directly Couple Label-Free Optical Sensing Technology with Mass Spectrometry for Top-Down Protein Analysis", ChemRxiv, Oct. 21, 2022, 22 pages.

* cited by examiner

β-Amyloid 1-40 Samples (Sensorgrams Top to Down):
3.3 µg/ml; 1.1 µg/ml; 0.37 µg/ml; 0.12 µg/ml

MICROPROBE-CAPTURE IN-EMITTER ELUTION-ELECTROSPRAY IONIZATION

CROSS-REFERENCING

This application claims the benefit of U.S. provisional application Ser. No. 63/324,573, filed on Mar. 28, 2022, which application is incorporated by reference herein in its entirety.

BACKGROUND

The study of biomolecular interactions is an essential foundation of modern life and medical sciences. It provides fundamental explanations to biological functions and is essential for understanding cellular signal transduction, metabolism regulation, and cell cycles. Label-free technologies are major tools used to study biomolecular interactions.[1]

Label-free technologies sense the refractive index change or optical thickness change caused by biomolecular interactions such as antibody-antigen binding, achieving real-time measurement without employing a reporter molecule (enzyme, fluorophore, etc.) attached to the biomolecules. The recorded time course of biomolecular complex formation provides the interaction characteristics such as kinetic and affinity constants.

Classical label-free technologies such as surface plasmon resonance (SPR) typically rely on complicated fluidic systems for sample delivery and their applicability in clinical laboratories is limited. The development of label-free technologies in the past decade has advanced from fluidics-based sensing chips into the era of dip-in-solution sensing probes, which have the flexibility to work with various sample types such as body fluids, tissue extracts, etc. A new technology of this kind is called thin-film interferometry (TFI) or next-generation biolayer interferometry (next-gen BLI). It utilizes biomolecule-coated quartz-glass sensing probes to measure biomolecular interactions on the sensing probe tips. The signal acquisition is compatible with the format of conventional microtiter plate immunoassays. Thus, in addition to the characterization of biomolecular interactions, TFI (next-gen BLI) can also be used to quantify biomolecules of interest, for instance the TFI-based clinical diagnostic assays for monoclonal antibody therapeutics and SARS-COV-2 antibodies.[2-4]

Although label-free analysis characterizes the kinetics and affinity of biomolecular interactions, they are not able to further analyze the interacting partners. Therefore, to identify or characterize the structural details of the biomolecules, label-free analysis must be coupled with another technology. An ideal technology to couple with label-free analysis is mass spectrometry (MS), which has been a central technology for structural analysis of biomolecules. However, there has not been an ideal coupling method for label-free analysis and MS, mainly due to low sample quantity-only a small number of biomolecules can be captured on the sensing probe tips. The previously reported coupling solutions included separate steps of elution from sensing probes and injection to MS, thus the experiment process was very complicated due to the necessity of extracting and concentrating dispersed analytes in the elution step.[5-7]

SUMMARY

Provided herein is a method for analyzing a molecular interaction. In some embodiments the method may comprise: capturing an analyte on a probe that comprises a binding agent, inserting the probe into the interior capillary of an electrospray emitter, releasing the analyte from the probe while it is in the emitter using an elution liquid, nebulizing the analyte by electrospray; and analyzing the nebulized analyte by mass spectrometry. In this description, the term "analyzing a molecular interaction" is intended to include, for example: (1) identifying one or more unknown binding partners involved in a molecular interaction, (2) quantifying one or more binding partners involved in a molecular interaction, and (3) characterizing one or more binding partners involved in a molecular interaction. Other uses may become apparent.

In some embodiments, the method (which may be referred to as microprobe-capture in-emitter elution-electrospray ionization (MPIE-ESI)) allows one to directly couple label-free analysis and MS, particularly between TFI-based label-free analysis and high-resolution MS (HR-MS). This coupling endows the power of MS-based identification of interacting partners to the label-free characterization of biomolecular interactions. A target of interest (analyte) is first captured on the surface of a sensing probe (microprobe) during label-free analysis, and then eluted from the microprobe inside an electrospray emitter and immediately sprayed into a mass spectrometer for HR-MS analysis. HR-MS provides superior resolution and can precisely identify small molecules, proteins, and nucleic acids. It can further unravel amino acid sequence of proteins and base sequence of nucleic acids. The capture of analytes on label-free sensing probes not only allows for real-time monitoring of the binding process through label-free analysis, but also purifies the targets of interest to reduce background noise in HR-MS analysis. In addition, label-free technologies incorporated highly optimized surface chemistry for capturing large biomolecules from complex matrices. The typical surface chemistry includes coating with a monolayer of thiols or silanes, covering with a layer of polysaccharides, and modifying the functional groups on the layers. The surface chemistry renders better performance than conventional biomolecule fishing tools such as beads and resins.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIG. 1A—Pictures of BLI microprobe, electrospray emitter, ESI ion source, and MPIE-ESI-MS interface under stereoscope. FIG. 1B—Illustration of running BLI-based affinity capture. FIG. 1C—Illustration of setting up the in-emitter elution ESI-MS.

FIG. 2A—A concentration series of Aβ 1-40 standard samples: sensorgrams obtained from the 4 microprobes measuring 4 samples at different concentrations (left); raw mass spectra and deconvoluted mass spectra of eluted Aβ 1-40 molecules from the 4 microprobes (right), showing Aβ 1-40 (4327.1 Da) and probably the sodium adduct of Aβ 1-40 (4349.1 Da). FIG. 2B—MS$^2$ analysis of the +4 precursor ion of Aβ 1-40 (m/z 1083.3) in a Aβ 1-40 standard sample: raw MS$^2$ mass spectrum (left) and deconvoluted MS$^2$ mass spectrum (right) of Aβ 1-40 fragments, showing the identified fragments of Aβ 1-40. FIG. 2C—Two normal CSF samples: raw mass spectra (left) and deconvoluted mass spectra (right) of eluted Aβ 1-40 molecules, demonstrating the capture and analysis of Aβ 1-40 in CSF.

FIG. 3A—A concentration series of Tf standard samples: sensorgrams obtained from the 5 microprobes measuring 5 samples at different concentrations (left); MS raw mass spectra and deconvoluted mass spectra of eluted Tf molecules from the 5 microprobes (right), showing the major serum Tf proteoform (79554 Da). FIG. 3B—A serum sample: raw mass spectrum (left) and deconvoluted mass spectrum (right) of eluted Tf molecules, showing the major (79554 Da) and minor serum Tf proteoforms. FIG. 3C—A CSF sample: raw mass spectrum (left) and deconvoluted mass spectrum (right) of eluted Tf molecules, showing the major (78008 Da) and minor brain Tf proteoforms in addition to the serum Tf proteoforms. The serum and CSF samples were drawn from the same individual.

DESCRIPTION OF EXEMPLARY EMBODIMENTS

Figures 1A, 1B:
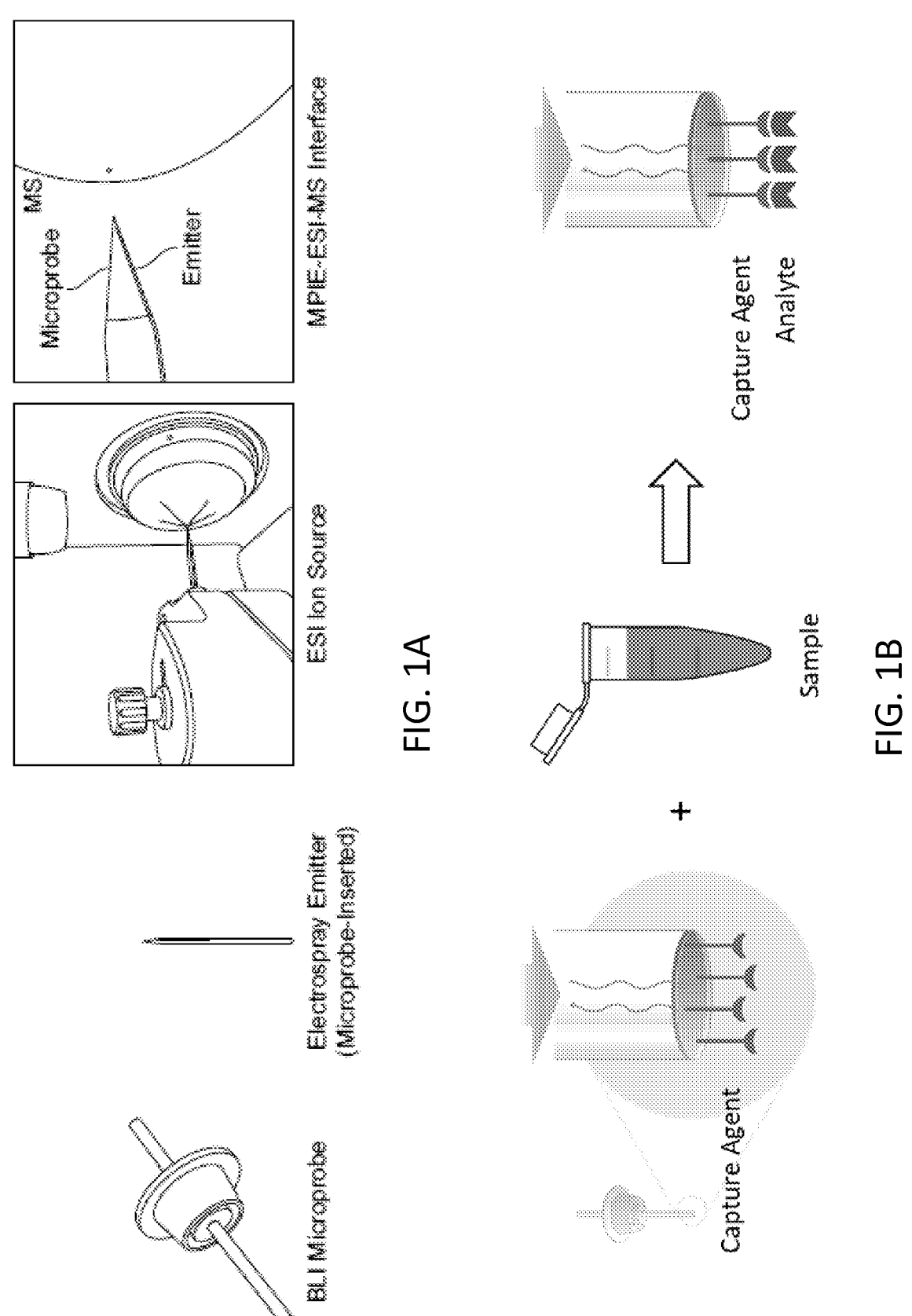
FIGS. 1A-1C.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

The headings provided herein are not limitations of the various aspects or embodiments of the invention. Accordingly, the terms defined immediately below are more fully defined by reference to the specification as a whole.

Provided herein is a method for analyzing a molecular interaction. In some embodiments the method may comprise: capturing an analyte on a probe that comprises a binding agent, inserting the probe into the interior capillary of an electrospray emitter, releasing the analyte from the probe while it is in the emitter using an elution liquid, nebulizing the analyte by electrospray; and analyzing the nebulized analyte by mass spectrometry.

In some embodiments, the probe is quartz glass, e.g., a thin-film interferometry (TFI) probe. In some embodiments, the method may comprise detecting binding of the analyte by the binding agent by thin-film interferometry. For example, in some cases the method involve measuring the kinetics of binding of the analyte to the binding agent by thin-film interferometry. TFI probes generally contain a glass rod having a diameter of less than 1 mm having specialized optical layers and specialized surface chemistry built at the distal end (the sensing end) of the probe. The probe is linked to a spectrophotometer and is capable of analyzing the interference pattern of white light reflected from an internal reference layer within a layer of immobilized biomolecules on the surface chemistry of the biosensor. Shifts in interference due to the accumulation of biomolecules are monitored in real-time to sensitively analyze and calculate rates of association and dissociation among target proteins with high precision. Thin-film interferometry (TFI) probes, systems containing the same and methods for their use are described in, e.g., US20110305599A1, Luo et al (Clin Chim Acta 2020 502:128-132), Luo et al (Clinical Infectious Diseases 2021 73: e3095-e3097) and Luo et al (Clin Chem 2020 66:1319-1328), which are incorporated by reference herein for disclosure of the probes, systems containing the same and methods.

A TFI microprobe pre-coated with a biomolecule can effectively enriching for interacting biomolecules in a biological sample with minimum non-specific binding. The label-free analysis further monitors the biomolecule fishing process, providing guidance to the biomolecule fishing experiment.

This application of the MPIE-ESI technique can be considered as an improvement to immunoprecipitation, the conventional method of biomolecule enrichment. In comparison to the conventional bead-based or resin-based immunoprecipitation methods, the unique values include: (1) As the analyte is eluted to immediately enter the electrospray nebula rather than being diluted in an elution sample, MPIE-ESI requires provides high sensitivity and minimal target quantity (<1 ng protein), thus trace samples can be analyzed; (2) the surface chemistry on the microprobe is optimized for mitigating non-specific binding of interferents, better than beads or resins used in immunoprecipitation; and (3) the biomolecule fishing process is monitored by label-free analysis which provides additional information of the target, such as captured amount and binding kinetics.

In any embodiment, the binding agent on the probe can be an antibody, e.g., a scFv or nanobody. However, other types of binding agent, e.g., aptamers, ligands, and other scaffolds can be used. The binding agent may be conjugated to the probe by any suitable method. In some embodiments, the probe may be treated so that it has reactive groups e.g., a hydroxyl, sulfhydryl, carboxy or amine group, to which the binding agent can be conjugated, either covalently or non-covalently. Conjugation methods are known. For example, the material can be modified to contain can comprise a variety of reactive groups, including, but not limited to, N-hydroxysuccinimidyl ester, sulfo-N-hydroxysuccinimidyl ester, a halo-substituted phenol ester, pentafluorophenol ester, a nitro-substituted phenol ester, an anhydride, isocyanate, isothiocyanate, an imidoester, maleimide, iodoacetyl, hydrazide, an aldehyde, or an epoxide. Other suitable groups are known in the art and may be described in, e.g., Hermanson, "Bioconjugate Techniques" Academic Press, 2nd Ed., 2008. The ligand can be produced separately and then conjugated to the reactive group using known chemistry. The ligand may additionally contain a spacer in some cases. In some embodiments, the ligand may be attached to the material via Click chemistry. As noted below, the binding agent can be attached to the probe via a biotin interaction.

The method described above can be employed to analyze one or more analytes from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the sample used in the method may be derived from a mammal, wherein certain embodiments the mammal is a human. In exemplary embodiments, the sample may be from a mammal, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample may be obtained from a cancer patient.

Exemplary utilities are described below.

Antibody Epitope Mapping

Epitope mapping identifies an antibody's binding site on its antigen, and it is a critical step in developing therapeutic and key reagent antibodies. Peptide scanning is a mainstream method for epitope mapping, which locates the binding site by testing antibody against a set of synthetic peptides designed from its antigen (as antigen fragments). This procedure is inefficient when it applies to a large-sized antigen because the antibody must be tested against a tremendous set of synthetic peptides in a one-by-one manner. When label-free analysis is coupled with MS, an antibody can be tested against a mixture of all peptides rather than single peptides, and the peptides captured by the antibody can be simultaneously identified by MS. Thus, the efficiency of peptide scanning can be substantially increased.

The concept of efficient peptide scanning using coupled label-free analysis and MS has been demonstrated. However, in this report the two technologies were not directly coupled, resulting in a highly complicated sample preparation procedure between label-free analysis and MS. In contrast, the MPIE-ESI technique directly couples label-free analysis and MS, which significantly simplifies the experiment, saving time and cost.

MHC-Binding Peptide Identification

The adaptive immune system is a key part of animal immune system, and it has always been a focus of modern medicine. A critical step in activating the adaptive immune system is the interaction between major histocompatibility complex (MHC) class II and peptides digested from exogenous pathogens. Identifying the peptides that bind to MHC molecules plays an important role in monitoring immune responses, understanding disease mechanisms, developing therapies and vaccines, etc.

The peptides binding to MHC molecules can be identified using coupled label-free analysis and MS. Similar to antibody epitope mapping, the workflow includes: (1) applying a microprobe pre-coated with MHC to a mixture of synthetic peptides designed from a pathogen; and (2) analyzing the captured peptides on the microprobe by MS. As the MPIE-ESI technique directly couples label-free analysis and MS, it can implement this experiment with simplicity and high efficiency.

Target Quantitation

MS has been widely used for quantitation of biomolecules including compounds, peptides, and proteins. To precisely quantify a target, sample preparation is necessary to clean up the sample and/or concentrate the analyte. "Fishing out" a target from complex sample matrix using an antibody is considered as a highly efficient sample preparation method for MS quantitation, which is called mass spectrometric immunoassay (MSIA).[8] MSIA is preferred in quantifying peptides and proteins. The drawbacks of MSIA include complicated experiment procedure, limited sensitivity due to sample dilution and/or sample loss during the delivery to a mass spectrometer, and non-specific binding of interferents. The MPIE-ESI technique can achieve the antibody-based target capture in the same way as MSIA, while it can overcome all the drawbacks by directly coupling two automated analytical platforms (label-free analysis and MS). This feature simplifies the experiment procedure, minimizes sample dilution and loss to enhance sensitivity, and utilizes optimized surface chemistry to mitigate non-specific binding of interferents. Therefore, the MPIE-ESI technique can be used to quantify low-abundance and challenging targets, such as Alzheimer's disease marker β-amyloid which is difficult to measure using traditional immunoassays due to its low abundance and high stickiness to other biomolecules.

This application of the MPIE-ESI technique results in a novel option of MS-based target quantitation, which may provide irreplaceable value to some specific target quantitation needs.

Label-free analysis is commonly used to analyze binding kinetics of biomolecular interactions, in which the association and dissociation between the interacting partners are measured to calculate their binding rate and affinity constants. To implement kinetic analysis, one interacting partner (ligand) is immobilized on a microprobe and the other interacting partner (analyte) is present in a solution. Although the kinetic analysis can be completed using label-free analysis, it does not tell if a protein analyte is a single proteoform or a mixture of proteoforms or structural analogs. The MPIE-ESI technique directly couples label-free analysis and MS, facilitating the identification of interacting partners at the same time of label-free characterization of a biomolecular interaction.

This application of the MPIE-ESI technique provides a novel way to characterize biomolecular interactions while identifying interacting partners, which provides irreplaceable value for biological research. In comparison to the reported indirect coupling between label-free analysis and MS,[5-7] the unique value of the MPIE-ESI technique is "direct coupling", which allows for simple experiment procedure and results in high sensitivity.

In some embodiments, the elution liquid comprises a solvent.

In some embodiments, the releasing and nebulizing are done in the presence of a sheath fluid.

In some embodiments, the mass spectrometry is a high resolution mass spectrometry, e.g., time of flight (TOF), Orbitrap or FT-ICR mass spectrometer.

In some embodiments, the method may comprise, prior to step (b): dipping the probe into a sample that comprises analytes; washing the probe to remove unbound analytes; and detecting binding of analytes to the probe by thin-film interferometry.

In some embodiments, the elution liquid is delivered by a capillary that is operably connected to capillary of the emitter.

In some embodiments, the binding agent is an antibody. In these embodiments, the analyte may comprise one or more epitopes for the antibody.

In some embodiments, the binding agent is MHC protein. In these embodiments, the analyte may comprise one or more peptide fragments.

An apparatus is also provided. In some embodiments, the apparatus may comprise: an electrospray emitter having an interior capillary; and a thin-film interferometry (TFI) probe comprising a binding agent thereon, wherein the probe fits into the interior capillary of the emitter.

In these embodiments, the emitter may operably connected to a reservoir of elution liquid.

In these embodiments, the apparatus may further comprise a mass spectrometer and/or a spectrophotometer.

EXAMPLE

This disclosure provides a new affinity capture technique for top-down protein analysis, referred to as microprobe-capture in-emitter elution (MPIE), which enables direct coupling of next-generation BLI with MS. To implement MPIE, an analyte is first captured on the surface of a microprobe, and subsequently eluted from the microprobe inside an electrospray emitter. The capture process is monitored in real-time via BLI. When electrospray is established from the emitter to a mass spectrometer, the analyte is immediately ionized via electrospray ionization (ESI) for HR-MS analysis. By this means, BLI and HR-MS are directly coupled in the form of MPIE-ESI-MS, which can add significant value to MS, or more specifically, TD-MS since affinity capture is typically applied to protein analytes and enzymatic digestion is not included.

Exemplary Instrumentation

A TFI (next-gen BLI) Gator Plus label-free analyzer (Gator Bio, Palo Alto, CA) was used to capture an analyte on a microprobe (Gator Bio, Palo Alto, CA). The microprobe was pre-coated with streptavidin, and then loaded with biotinylated anti-transferrin antibody (anti-Tf Ab). (The microprobe was pre-coated with anti-Fab Ab for anti-A1c Fab analysis.)

An Orbitrap Q-Exactive Plus mass spectrometer (Thermo Scientific, San Jose, CA) was coupled with an ECE-001 capillary electrophoresis (CE) unit through an EMASS-II ion source (CMP Scientific, Brooklyn, NY). A neutrally coated fused-silica capillary (360 μm O.D., 50 μm I.D., 100 cm) was used to deliver elution liquid to the microprobe. An electrospray emitter is 1 mm O.D. and 0.75 mm I.D., with a tip orifice size of 20-30 μm (CMP Scientific, Brooklyn, NY). The elution liquid was acetonitrile:water 4:1 with 2% formic acid. The sheath liquid for electrospray ionization (ESI) was 10 mM ammonium formate in water. ESI voltage was set at 2.2 kV. The electrospray emitter was placed 1 mm away from the mass spectrometer inlet.

The Orbitrap mass spectrometer was connected to the CE unit through a contact closure cable, which transmitted contact closure signals to trigger MS data acquisition. In the mass spectrometer, the ion-transfer capillary temperature was set at 350° C. for Tf analysis (320° C. for anti-A1c Fab analysis). In full-scan mode, mass spectra were acquired in positive polarity from 1000 m/z to 3500 m/z at resolution 17500 for Tf analysis (1200 m/z to 3300 m/z at resolution 140000 for anti-A1c Fab analysis), and the number of microscans was set at 10.

The experiment protocol may involve the following steps.
(1) Fill a capillary with elution liquid.
(2) Apply a microprobe to a sample dissolved in PBST (PBS with 0.05% Tween 20) to capture an analyte, and then place the microprobe in PBST to rinse off non-specific binders.
(3) Load 100 μl sheath liquid in a 1.5 ML tube, and soak the microprobe in the solution for 30 s while gently shaking.
(4) Fill an electrospray emitter with sheath liquid.
(5) Insert the microprobe in the emitter, and insert the capillary right behind the microprobe.
(6) Turn on ESI, and inject elution liquid to elute the analyte from the microprobe inside the emitter. The analyte is directly sprayed into a mass spectrometer.

Materials and Methods

Materials and Samples: LC-MS grade water, acetonitrile, and formic acid were purchased from Thermo Fisher Scientific (Waltham, MA). β-Amyloid (Aβ) 1-40 standard was purchased from Abcam (Cambridge, UK), and a biotinylated mouse monoclonal anti-Aβ IgG antibody (anti-Aβ Ab) from Biolegend (San Diego, CA). Human transferrin (Tf) standard (Tf purified from human serum) was purchased from Sigma-Aldrich (St. Louis, MI), and a mouse monoclonal anti-transferrin IgG antibody (anti-Tf Ab) from Sinobiological (Wayne, PA), and biotinylated using EZ-Link NHS-PEG4-Biotin from Thermo Fisher Scientific (Waltham, MA). Remnant cerebrospinal fluid (CSF) and serum samples from general patients were obtained from Stanford Health Care, following approved IRB protocols for the use of remnant patient specimens.

Sample Preparation Aβ 1-40 and Tf were used as model protein targets to study the performance of MPIE-ESI-MS. The Aβ 1-40 standard was first dissolved in DMSO and then diluted in phosphate-buffered saline at pH 7.4 with 0.02% Tween 20, 0.05% sodium azide, and 0.2% BSA (PBST-B) to make a concentration series of Aβ 1-40 standard samples. The Tf standard was first dissolved in phosphate-buffered saline at pH 7.4 with 0.02% Tween 20 and 0.05% sodium azide (PBST), and then diluted in PBST to make a concentration series of Tf standard samples. The capture agents anti-Aβ Ab and anti-Tf Ab were diluted in PBST-B to 10 μg/ml for use. The Aβ 1-40 standard samples were prepared right before use. For Aβ analysis, CSF samples were 1:1 diluted in PBST-B. For Tf analysis, CSF samples were 1:1 diluted in PBST and serum samples were 1:19 diluted in PBST.

Figure 1C:
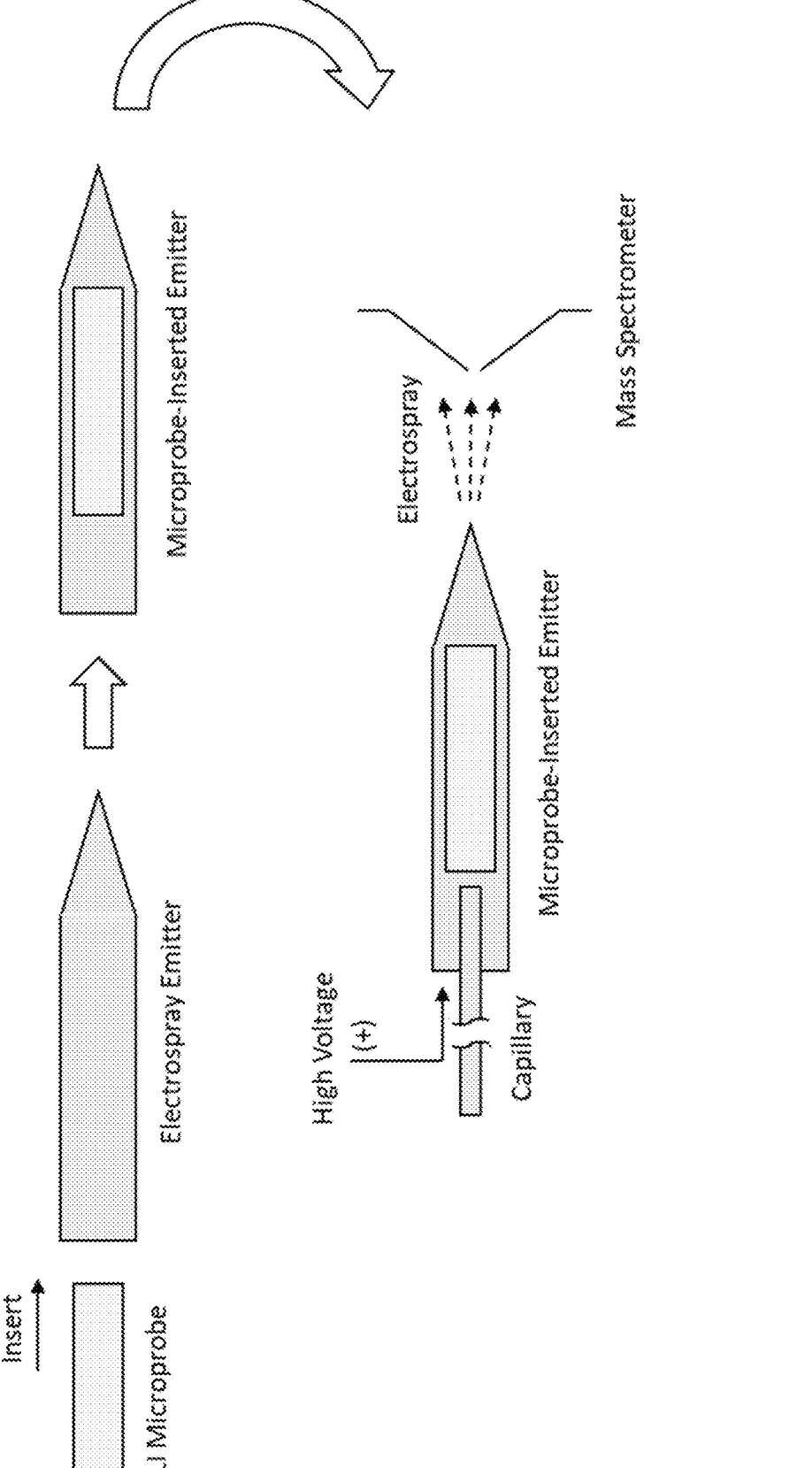

MPIE-ESI-MS Experiment: An MPIE-ESI-MS experiment consists of two parts: BLI-based affinity capture and in-emitter elution ESI-MS. The BLI-based affinity capture was carried out in 3 steps: (1) a BLI microprobe pre-coated with streptavidin was dipped into a capture agent (anti-Aβ Ab or anti-Tf Ab) solution for 10 min to load the capture agent; (2) the microprobe was dipped into a sample for 10 min to capture the corresponding analyte (Aβ or Tf), and then rinsed in the running buffer (PBST-B for Aβ analysis or PBST for Tf analysis) for 1 min to remove non-specifically bound molecules. The in-emitter elution ESI-MS was carried out in 6 steps: (1) an electrospray emitter was filled with a sheath liquid (10 mM ammonium formate in water); (2) after affinity capture, the microprobe was rinsed in the sheath liquid for 10 s, inserted into the emitter through the regular open end, and settled in the tapered end by gravity; (3) the emitter was mounted to the ESI ion source; (4) the elution liquid-delivering capillary was inserted into the emitter through the regular open end and positioned right behind the microprobe; (5) a positive voltage was applied to the sheath liquid in the emitter to establish electrospray; (6) MS data acquisition was initiated, and injection of the elution liquid was started subsequently. The emitter was placed ~2 mm away from the mass spectrometer inlet with the electrospray voltage set at 2.2 kV. The injection of the elution liquid was driven by 5 psi of pneumatic pressure. The parts described above are shown in FIG. 1A. The procedures of running BLI-based affinity capture and setting up the in-emitter elution ESI-MS are illustrated in FIG. 1B and FIG. 1C, respectively.

The BLI-based affinity capture was implemented in a Gator Plus analyzer (Gator Bio, Palo Alto, CA). Cylindrical quartz-glass BLI microprobes with 1 mm diameter were used. The in-emitter elution ESI-MS was implemented in an EMASS-II ESI ion source which coupled an ECE-001 capillary electrophoresis (CE) instrument (CMP Scientific, Brooklyn, NY) with an Orbitrap Q-Exactive Plus mass spectrometer (Thermo Fisher Scientific, San Jose, CA). A glass electrospray emitter with 1.5 mm O.D. and 1.17 mm I.D. (CMP Scientific, Brooklyn, NY) was used for MPIE, which has a regular open end and a tapered open end (tip orifice diameter 20-30 μm). A fused-silica capillary (360 μm O.D., 50 μm I.D., 100 cm) was used to deliver an elution liquid (80% acetonitrile and 2% formic acid in water) into the emitter, was employed to carry out MS analysis.

The MS parameters for Aβ analysis were ion-transfer capillary temperature 320° C., S-lens RF level 50, and number of microscans 5. Full MS dd-MS$^2$ mode was applied: primary mass spectra acquired in positive polarity at resolution 140K; stepped normalized collision energy 20, 30, and 40 for fragmentation; secondary mass spectra acquired for the top 5 abundant precursor ions at resolution 70K. When analyzing CSF samples, targeted-SIM dd-MS$^2$ mode was used to increase the analytical sensitivity. The isolation window was set at m/z 4.0 and the number of microscans was increased to 10. The MS parameters for Tf analysis were ion-transfer capillary temperature 350° C., S-lens RF level 50, and number of microscans 10. Primary mass spectra were acquired in positive polarity at resolution 17.5K.

Data Analysis The acquired data in each MPIE-ESI-MS experiment was viewed as a time trace of MS responses, and the elution time window of an analyte was identified by checking the molecular ions of the analyte at each time point. The data in the elution time window were selected for deconvolution using Biopharma Finder 4.1 (Thermo Fisher Scientific, San Jose, CA), employing the Xtract algorithm for Aβ analysis and the ReSpect algorithm for Tf analysis. MS peaks of analytes were displayed in deconvoluted spectra in their uncharged state, showing monoisotopic molecular masses through the Xtract algorithm and average molecular masses through the ReSpect algorithm.

Results and Discussion

Figure 2A:
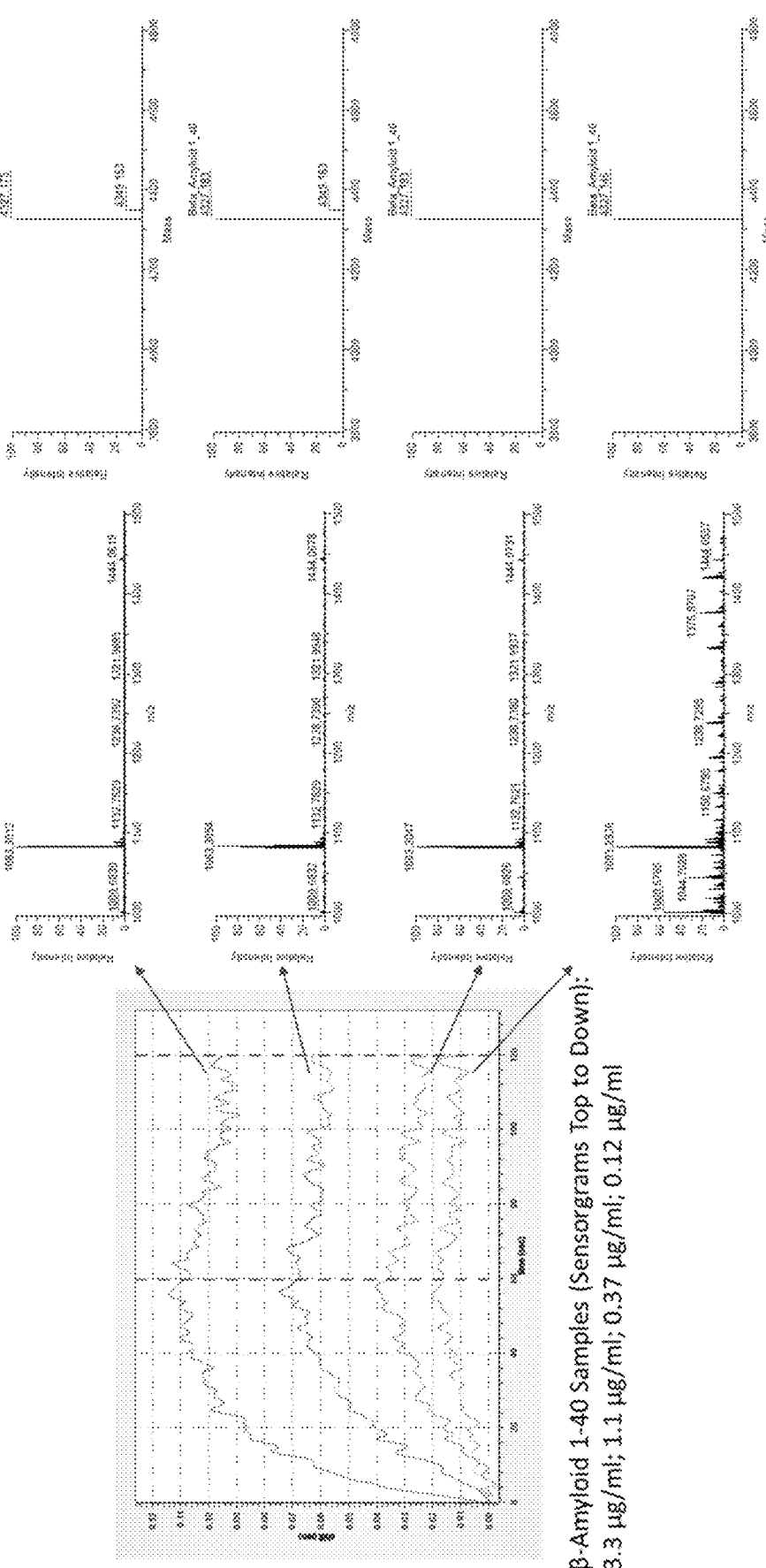
FIGS. 2A-2C. MPIE-ESI-MS analysis of Aβ 1-40.
Figure 2B:
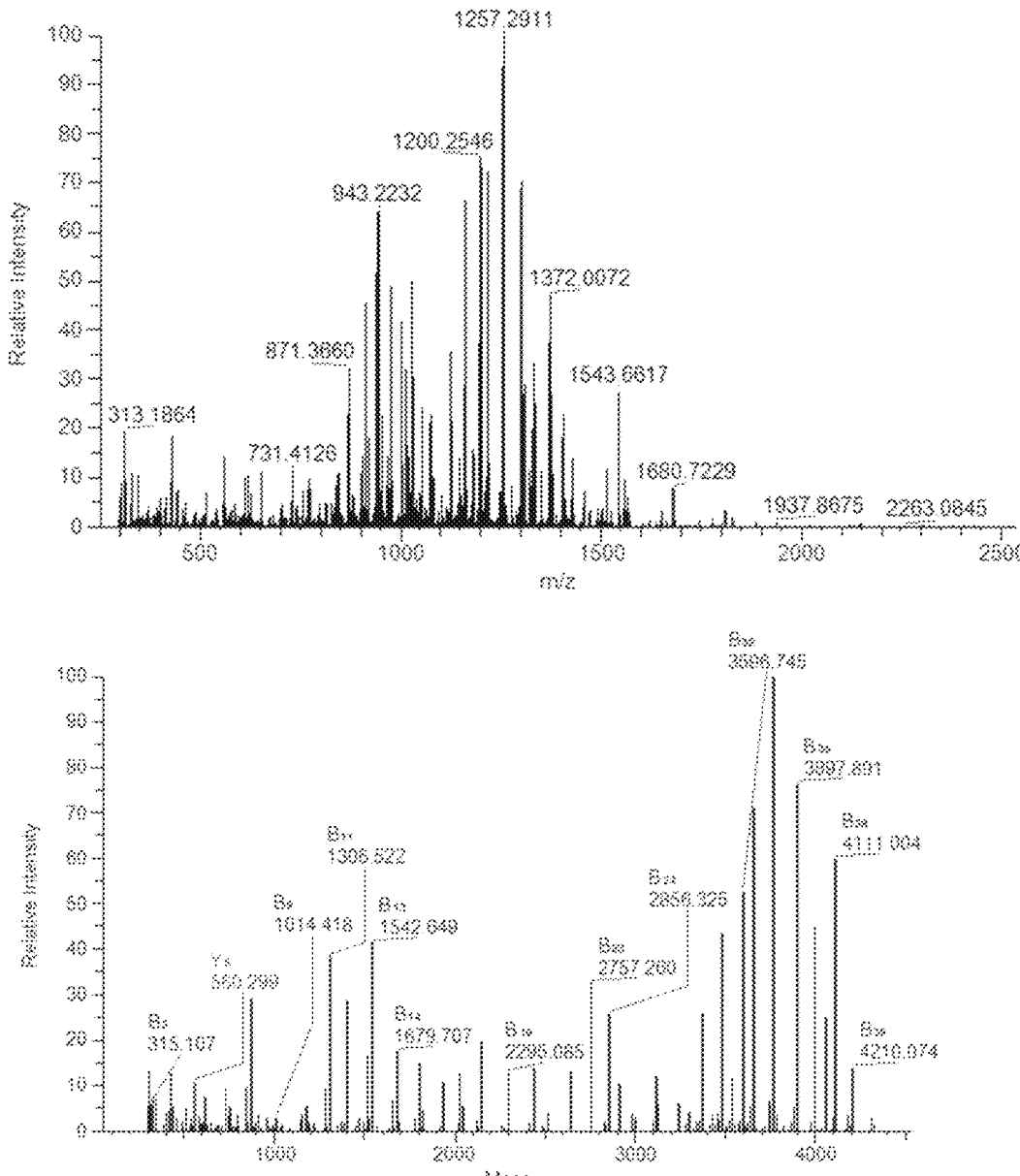
Figure 3A:
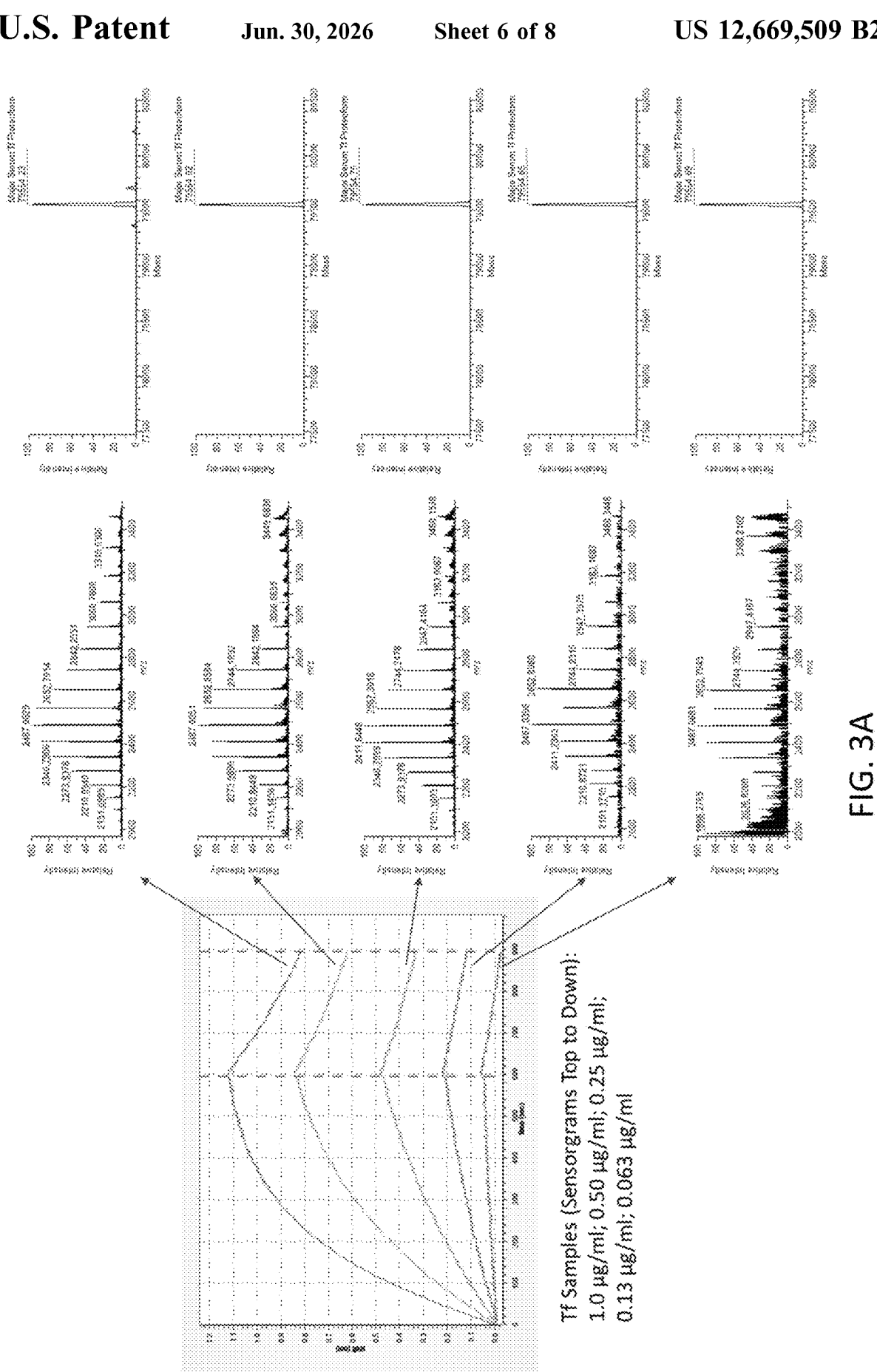
FIGS. 3A-3C. MPIE-ESI-MS analysis of Tf.

The performance of MPIE-ESI-MS was demonstrated by the analysis of Aβ 1-40 and Tf, which are typical human proteins used as clinical diagnostic markers. Aβ 1-40 is a 40-amino acid small protein (or peptide) closely related to Alzheimer's disease.[13] Tf is a 679-amino acid glycosylated large protein that plays an essential role in iron metabolism, and its proteoforms are used to diagnose CSF leak.[14] A concentration series of Aβ 1-40 standard samples at 3.3, 1.1, 0.37, and 0.12 μg/ml were analyzed by MPIE-ESI-MS, as shown in FIG. 2A. Similarly, a concentration series of Tf standard samples at 1.0, 0.50, 0.25, 0.13 μg/ml, and 0.063 μg/ml were analyzed by MPIE-ESI-MS, as shown in FIG. 3A. In both cases a blank sample (running buffer) was employed as both the reference for the label-free optical sensing measurement and the negative control for the MS analysis. Real-time monitoring of affinity capture process was implemented in the next-generation BLI analyzer, and the reference-subtracted time traces of label-free optical sensing responses (sensorgrams) were obtained. The sensorgrams showed the association phase (analyte-capturing phase) and dissociation phase (sensing surface rinsed in the running buffer). The intact-protein MS analysis of Aβ 1-40 standard samples showed a dominant MS peak at 4327.1 Da and that of Tf standard samples showed a dominant MS peak at 79554 Da in deconvoluted mass spectra. The blank samples revealed only noise in the raw mass spectra and no MS peak could be resolved after deconvolution. In the Aβ 1-40 analysis, the dominant analyte should be Aβ 1-40 as the measured molecular mass (monoisotopic mass) matched the theoretical molecular mass 4327.148 Da calculated from its primary structure. The assignment could be confirmed by MS$^2$ fragmentation: the MS$^2$ analysis of the +4 precursor ion of Aβ 1-40 (m/z 1083.3) in an Aβ 1-40 standard sample is shown in FIG. 2B. In the deconvoluted MS$^2$ mass spectrum, 37 b-fragments and 9 y-fragments were identified by matching their masses to the predicted fragments derived from the amino acid sequence of Aβ 1-40, resulting in a sequence coverage of 95%. Moreover, a minor MS peak at 4349.1 Da was observed in some deconvoluted mass spectra, which was probably the sodium adduct of Aβ 1-40. In the Tf analysis, since it is known that a tetrasialo-Tf proteoform predominates in normal human serum and the Tf standard was purified from human serum, the dominant analyte was likely the major serum Tf proteoform as the measured molecular mass (average mass) matched the theoretical mass 79554.71 Da calculated from its primary structure with the reported N-glycans of the tetrasialo-Tf.[15-16] Note that the eluted Tf molecules were denatured and iron-free since a protein-denaturing elution liquid was used.

In the past, limited capture capacity of label-free optical sensing devices was a major barrier that hindered the combination of label-free optical sensing technologies and MS. Because only a minute amount of analyte (one layer of molecules) could be captured on the surface of a microprobe, the captured analyte must be eluted into a small volume of solution to make enough concentration for MS analysis. Therefore, the use of the particular electrospray emitter was crucial to MPIE-ESI-MS: the captured analyte on a microprobe was eluted into a tiny space at the tapered end of the electrospray emitter, which has a calculated volume of about 0.8 μl based on the dimensions; the tiny space enforced restricted dispersion of eluted analyte, enhancing the analytical sensitivity of the subsequent MS analysis. As demonstrated in FIG. 3A, the limit of detection for the Tf standard was at least 0.063 μg/ml, which corresponded to a saturation rate of anti-Tf Ab at 17% (calculation in supporting information). Provided that there was one layer of anti-Tf Ab molecules on the surface of a microprobe to capture Tf molecules and the maximum density for a typical protein on a label-free optical sensing surface is 1-2 ng/mm$^{2,17}$ the amount of anti-Tf Ab on a microprobe (tip area 4 mm$^2$) should be within 40 fmol and the captured Tf molecules should be no more than 7 fmol, which was an very low quantity. However, the 7 fmol Tf molecules would make a concentration of about 8 nM after dispersed in the tapered end of the electrospray emitter, resulting in a decent analyte concentration for MS analysis. The feature of restricted dispersion of eluted analyte in MPIE-ESI-MS substantially brings up the concentration of the minute amount of analyte captured by a BLI microprobe, allowing for the successful coupling of a label-free optical sensing technology with MS with good analytical sensitivity.

A sensorgram not only indicates the amount of the analyte captured on a microprobe, but it can also be fitted to the Langmuir molecular interaction model to obtain the kinetic and affinity constants between the two binding partners (Langmuir model explained in supporting information).[18] Using the sensorgrams in FIG. 2A and FIG. 3A, the association kinetic constants ($k_a$) and dissociation kinetic constants ($k_d$) could be measured, and the affinity constant (dissociation equilibrium constant $K_D$) could be calculated from the measured kinetic constants. Regarding the binding pair of anti-Aβ Ab and Aβ 1-40, $k_a$ was $7.4 \times 10^5$ M$^{-1}$s$^{-1}$, $k_d$ was $4.9 \times 10^{-3}$ s$^{-1}$, and $K_D$ was $6.6 \times 108$ M. Regarding the binding pair of anti-Tf Ab and Tf, $k_a$ was $2.8 \times 10^5$ M$^{-1}$s$^{-1}$, $k_d$ was $1.1 \times 10^{-3}$ s$^{-1}$, and $K_D$ was $3.9 \times 10^{-9}$ M. The affinity constants were in the regular range of mouse monoclonal antibodies, and consistent with the knowledge that antibodies bind more strongly to larger-sized antigens.

Figure 2C:
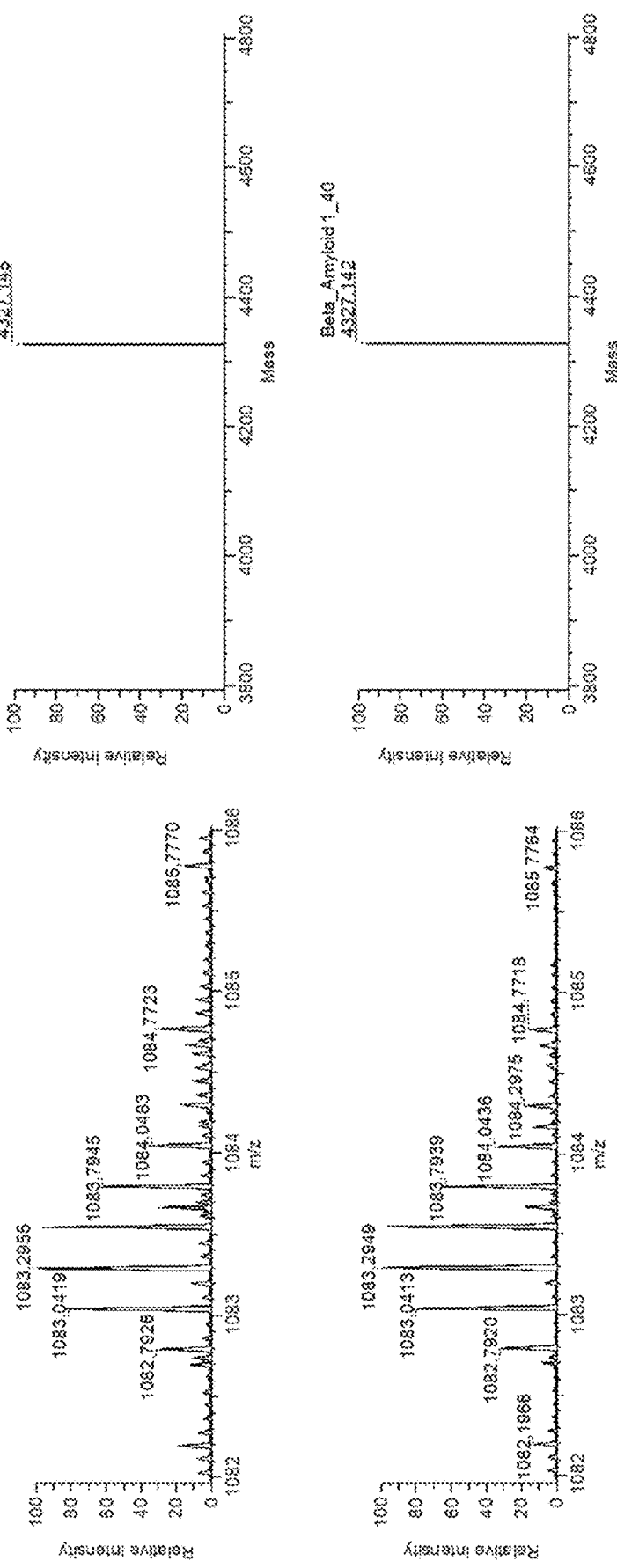
Figure 3B:
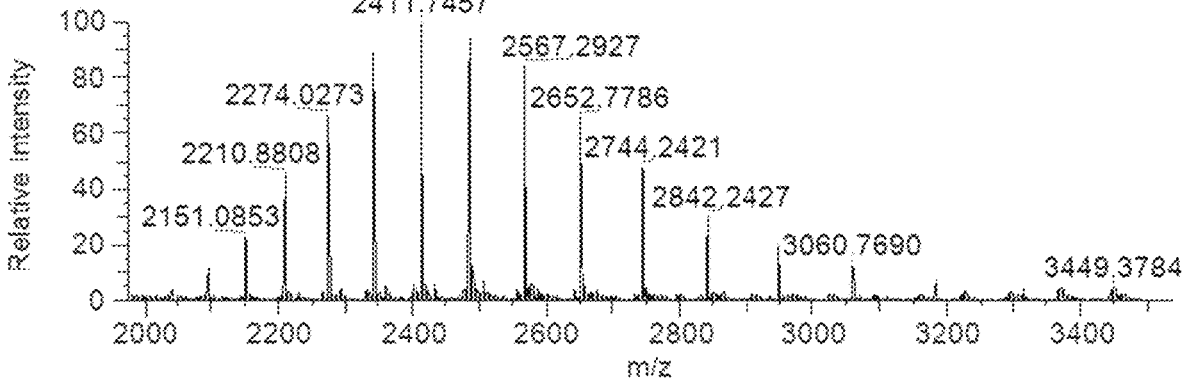
Figure 3B:
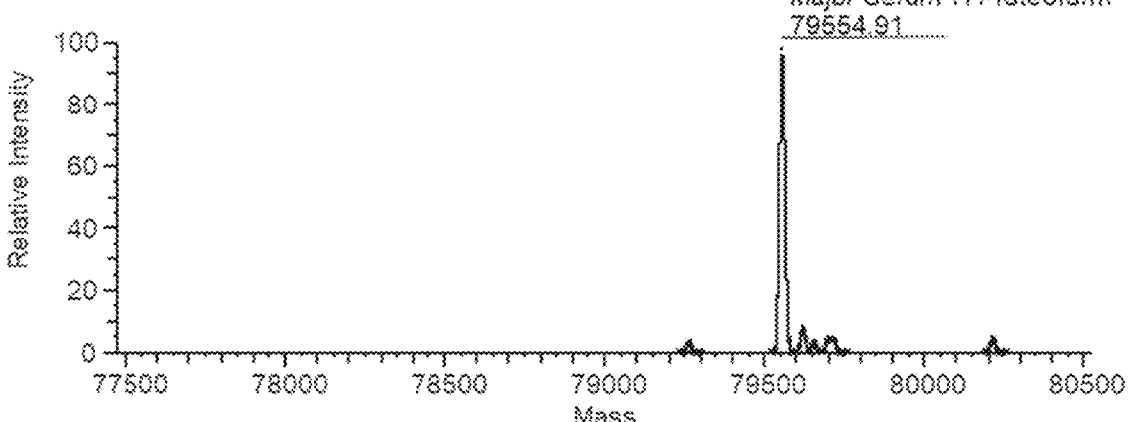
Figure 3C:
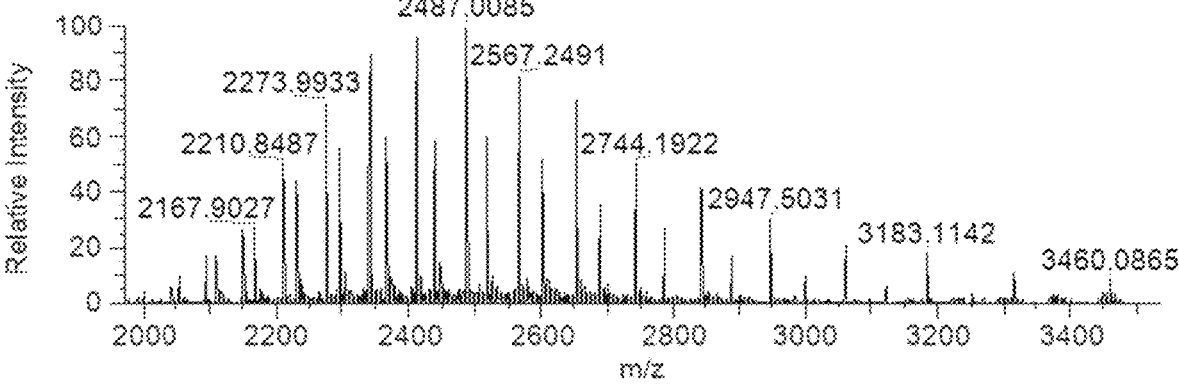
Figure 3C:
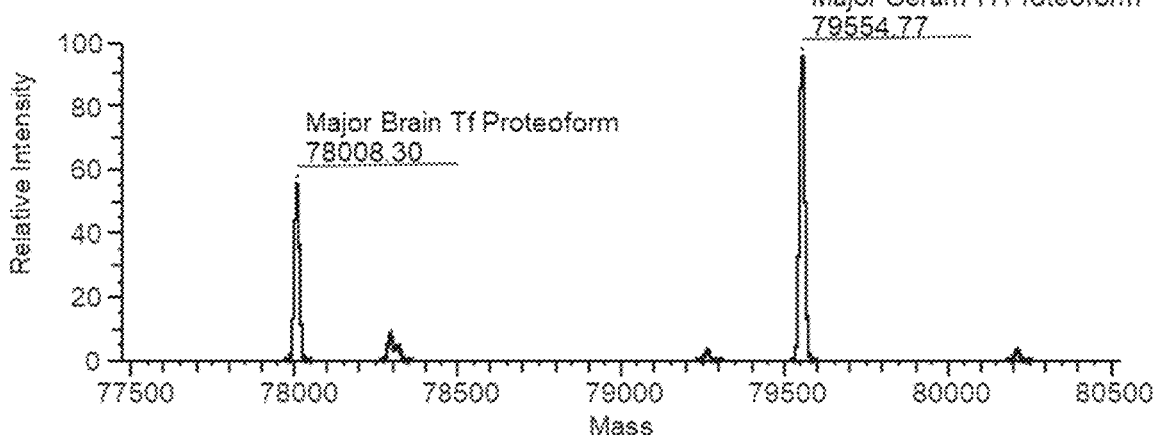

MPIE-ESI-MS was applied to human specimens to evaluate its applicability to clinical diagnostics. For Aβ 1-40 analysis, two normal CSF samples drawn from individuals without Alzheimer's disease were tested. Given the normal Aβ 1-40 concentration in CSF at the level of 10 ng/ml and the affinity constant ($K_D$) of the binding pair at $6.6 \times 10^{-8}$ M, 19 the saturation of anti-Aβ Ab was around 3.4% (calculation in supporting information). As the low saturation rate of capture agent limited the amount of Aβ 1-40 captured on the microprobes, targeted-SIM dd-MS$^2$ mode was used to increase the analytical sensitivity of the MS analysis. Aβ 1-40 was successfully detected in the two normal CSF samples, as shown in FIG. 2C. For Tf analysis, a serum sample and a CSF sample drawn from the same individual were tested. In FIG. 3B, the deconvoluted mass spectrum of the serum sample showed a dominant MS peak at 79554 Da and small MS peaks around 79554 Da. The MS peaks should be mainly serum Tf proteoforms and the dominant MS peak at 79554 Da was the major serum Tf proteoform, consistent with that measured from the Tf standard samples. In FIG. 3C, the deconvoluted mass spectrum of the CSF sample showed a significant MS peak at 78008 Da and small MS peaks close to 78008 Da, in addition to the serum Tf proteoforms. The MS peaks around 78008 Da should be mainly brain Tf proteoforms, consistent with the reports that two types of Tf proteoforms (serum and brain) are present in CSF.[20,21] The test results of the human specimens demonstrated that MPIE-ESI-MS has the potential to be used as a clinical diagnostic tool.

It should be noted that the capture agents in MPIE are not limited to antibodies. Other biologics that bind to a specific target with sufficient affinity can be used, such as lectins or enzymes. It was demonstrated in the analysis of Aβ 1-40 and Tf that binding characteristics of the binding pair (capture agent and analyte) could be obtained together with the MS analysis of the analyte in a single MPIE-ESI-MS experiment. Combining the binding characteristics with the structural information obtained from MS analysis can add significant value to the study of unknown targets. In addition, as label-free optical sensing devices are equipped with optimal surface chemistry to mitigate non-specific binding of interferents,[17,22] the performance of affinity capture in MPIE is more advantageous than the conventional affinity capture techniques. Thus, MPIE-ESI-MS can be a useful tool for biological research.

The foregoing description demonstrates that the affinity capture technique MPIE can directly couple a label-free optical sensing technology (next-generation BLI) with MS. The employment of next-generation BLI brings unique advantages to top-down protein analysis: (1) BLI allows for effective step-by-step optimization of affinity capture conditions without requiring MS analysis; (2) real-time monitoring of affinity capture process provides an estimated amount of captured analyte for every sample, serving as a means of quality control; (3) captured analyte is eluted into a tiny space at the tapered end of the electrospray emitter to enhance the analytical sensitivity of MS analysis. In comparison to the conventional affinity capture techniques such as bead-based immunoprecipitation, MPIE innovates the affinity capture methodology by introducing real-time process monitoring and providing binding characteristics of analytes, offering more information-rich experimental results. Thus, MPIE is a valuable addition to the TD-MS sample preparation toolbox, and more applications of MPIE-ESI-MS in top-down protein analysis are expected.

REFERENCES (1) Catherman, A. D.; Skinner, O. S.; Kelleher, N. L. Top Down Proteomics: Facts and Perspectives. *Biochemical and Biophysical Research Communications* 2014, 445 (4), 683-693.

(2) Tiambeng, T. N.; Tucholski, T.; Wu, Z.; Zhu, Y.; Mitchell, S. D.; Roberts, D. S.; Jin, Y.; Ge, Y. Analysis of Cardiac Troponin Proteoforms by Top-down Mass Spectrometry. In *Methods in Enzymology; Elsevier,* 2019; Vol. 626, pp 347-374.

(3) Luo, R. Y.; Wong, C.; Xia, J. Q.; Glader, B. E.; Shi, R.-Z.; Zehnder, J. L. Neutral-Coating Capillary Electrophoresis Coupled with High-Resolution Mass Spectrometry for Top-Down Identification of Hemoglobin Variants. *Clinical Chemistry* 2022, hvac171.

(4) Donnelly, D. P.; Rawlins, C. M.; DeHart, C. J.; Fornelli, L.; Schachner, L. F.; Lin, Z.; Lippens, J. L.; Aluri, K. C.; Sarin, R.; Chen, B.; Lantz, C.; Jung, W.; Johnson, K. R.; Koller, A.; Wolff, J. J.; Campuzano, I. D. G.; Auclair, J. R.; Ivanov, A. R.; Whitelegge, J. P.; Paša-Tolić, L.; Chamot-Rooke, J.; Danis, P. O.; Smith, L. M.; Tsybin, Y. O.; Loo, J. A.; Ge, Y.; Kelleher, N. L.; Agar, J. N. Best Practices and Benchmarks for Intact Protein Analysis for Top-down Mass Spectrometry. *Nat Methods* 2019, 16 (7), 587-594.

(5) Padula, M.; Berry, I.; O'Rourke, M.; Raymond, B.; Santos, J.; Djordjevic, S. P. A Comprehensive Guide for Performing Sample Preparation and Top-Down Protein Analysis. *Proteomes* 2017, 5 (4), 11.

(6) Trenchevska, O.; Nelson, R.; Nedelkov, D. Mass Spectrometric Immunoassays in Characterization of Clinically Significant Proteoforms. *Proteomes* 2016, 4 (1), 13.

(7) Sun, Y.-S. OPTICAL BIOSENSORS FOR LABEL-FREE DETECTION OF BIOMOLECULAR INTERACTIONS. *Instrumentation Science & Technology* 2014, 42 (2), 109-127.

(8) Luo, Y. R.; Chakraborty, I.; Lazar-Molnar, E.; Wu, A. H. B.; Lynch, K. L. Development of Label-Free Immunoassays as Novel Solutions for the Measurement of Monoclonal Antibody Drugs and Antidrug Antibodies. *Clinical Chemistry* 2020, 66 (10), 1319-1328.

(9) Luo, Y. R.; Yun, C.; Chakraborty, I.; Wu, A. H. B.; Lynch, K. L. A SARS-COV-2 Label-Free Surrogate Virus Neutralization Test and a Longitudinal Study of Antibody Characteristics in COVID-19 Patients. *J Clin Microbiol* 2021, 59 (7).

(10) Jung, V.; Roger, K.; Chhuon, C.; Pannetier, L.; Lipecka, J.; Gomez, J. S.; Chappert, P.; Charbit, A.; Guerrera, I. C. BLI-MS: Combining Biolayer Interferometry and Mass Spectrometry. *Proteomics* 2022, 2100031.

(11) Machen, A. J.; O'Neil, P. T.; Pentelute, B. L.; Villar, M. T.; Artigues, A.; Fisher, M. T. Analyzing Dynamic Protein Complexes Assembled On and Released From Biolayer Interferometry Biosensor Using Mass Spectrometry and Electron Microscopy. *JoVE* 2018, No. 138, 57902.

(12) Zhang, G.; Li, C.; Quartararo, A. J.; Loas, A.; Pentelute, B. L. Automated Affinity Selection for Rapid Discovery of Peptide Binders. *Chem. Sci.* 2021, 12 (32), 10817-10824.

(13) Murphy, M. P.; LeVine, H. Alzheimer's Disease and the Amyloid-β Peptide. *JAD* 2010, 19 (1), 311-323.

(14) Papadea, C.; Schlosser, R. J. Rapid Method for B2-Transferrin in Cerebrospinal Fluid Leakage Using an Automated Immunofixation Electrophoresis System. *Clinical Chemistry* 2005, 51 (2), 464-470.

(15) de Jong, G.; van Eijk, H. G. Microheterogeneity of Human Serum Transferrin: A Biological Phenomenon Studied by Isoelectric Focusing in Immobilized PH Gradients. *Electrophoresis* 1988, 9 (9), 589-598.

(16) de Jong, G.; van Noort, W. L.; van Eijk, H. G. Carbohydrate Analysis of Transferrin Subfractions Isolated by Preparative Isoelectric Focusing in Immobilized PH Gradients. *Electrophoresis* 1992, 13 (1), 225-228.

(17) *Handbook of Surface Plasmon Resonance*; Schasfoort, R. B. M., Tudos, A. J., Eds.; RSC Pub: Cambridge, UK, 2008.

(18) *Label-Free Biosensors: Techniques and Applications,* 1st ed.; Cooper, M. A., Ed.; Cambridge University Press, 2009.

(19) Lehmann, S.; Dumurgier, J.; Ayrignac, X.; Marelli, C.; Alcolea, D.; Ormaechea, J. F.; Thouvenot, E.; Delaby, C.; Hirtz, C.; Vialaret, J.; Ginestet, N.; Bouaziz-Amar, E.; Laplanche, J.-L.; Labauge, P.; Paquet, C.; Lleo, A.; Gabelle, A.; for the Alzheimer's Disease Neuroimaging Initiative (ADNI). Cerebrospinal Fluid A Beta 1-40 Peptides Increase in Alzheimer's Disease and Are Highly Correlated with Phospho-Tau in Control Individuals. *Alz Res Therapy* 2020, 12 (1), 123.

(20) Hoffmann, A.; Nimtz, M.; Getzlaff, R.; Conradt, H. S. 'Brain-Type' N-Glycosylation of Asialo-Transferrin from Human Cerebrospinal Fluid. *FEBS Letters* 1995, 359 (2-3), 164-168.

(21) Hoshi, K.; Matsumoto, Y.; Ito, H.; Saito, K.; Honda, T.; Yamaguchi, Y.; Hashimoto, Y. A Unique Glycan-Isoform of Transferrin in Cerebrospinal Fluid: A Potential Diagnostic Marker for Neurological Diseases. *Biochimica et Biophysica Acta (BBA)—General Subjects* 2017, 1861 (10), 2473-2478.

(22) Homola, J. Surface Plasmon Resonance Sensors for Detection of Chemical and Biological Species. *Chem. Rev.* 2008, 108 (2), 462-493.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

What is claimed is:

1. A method for analyzing a molecular interaction, comprising:
   (a) capturing an analyte on a quartz glass thin-film interferometry (TFI) probe that comprises a binding agent at one end of the probe;
   (b) inserting the entire probe into the interior capillary of an electrospray emitter that has a tip, wherein the inserting places the end of the probe that has the binding agent and analyte adjacent to the tip;
   (c) releasing the analyte from the probe while it is in the emitter using an elution liquid;

(d) nebulizing the analyte by electrospray from the tip of the electrospray emitter; and
   (e) analyzing the nebulized analyte by mass spectrometry.

2. The method of claim 1, further comprising detecting binding of the analyte by the binding agent by thin-film interferometry.

3. The method of claim 1, further comprising measuring the kinetics of binding of the analyte to the binding agent by thin-film interferometry.

4. The method of claim 1, wherein the elution liquid comprises a solvent.

5. The method of claim 1, wherein the releasing and nebulizing are done in the presence of a sheath fluid.

6. The method of claim 1, wherein the mass spectrometry is a high-resolution mass spectrometry.

7. The method of claim 6, wherein the analyzing of (e) is done by a time of flight (TOF), Orbitrap or FT-ICR mass spectrometer.

8. The method of claim 1, wherein the method comprises, prior to step (b):
   dipping the probe into a sample that comprises analytes;
   washing the probe to remove unbound analytes; and
   detecting binding of analytes to the probe by thin-film interferometry.

9. The method of claim 1, wherein the elution liquid is delivered by a capillary that is operably connected to capillary of the emitter.

10. The method of claim 1, wherein the binding agent is an antibody.

11. The method of claim 1, wherein the binding agent is an antibody and the analyte comprises one or more epitopes for the antibody.

12. The method of claim 1, wherein the binding agent is MHC protein.

13. The method of claim 12, wherein the analyte comprises one or more peptide fragments.

14. An apparatus comprising:
   an electrospray emitter having a tip and an interior capillary; and a quartz thin-film interferometry (TFI) probe comprising a binding agent thereon at one end of the probe; wherein the thin-film interferometry (TFI) probe is configured to fit entirely into the interior capillary of the electrospray emitter.

15. The apparatus of claim 14, wherein the emitter is operably connected to a reservoir of elution liquid.

16. The apparatus of claim 14, wherein the apparatus further comprises a mass spectrometer.

17. The apparatus of claim 14, wherein the apparatus further comprises a spectrophotometer.

* * * * *